United States Patent
Skurkovich et al.

(10) Patent No.: US 6,861,056 B2
(45) Date of Patent: Mar. 1, 2005

(54) COMPOSITIONS AND METHODS FOR TREATING HYPERIMMUNE RESPONSE IN THE EYE

(75) Inventors: Boris Skurkovich, Pawtucket, RI (US); Simon Skurkovich, Rockville, MD (US)

(73) Assignee: Advanced Biotherapy, Inc., Woodland Hills, CA (US)

(*) Notice: Subject to any disclaimer, the term of this patent is extended or adjusted under 35 U.S.C. 154(b) by 0 days.

(21) Appl. No.: 10/389,065

(22) Filed: Mar. 14, 2003

(65) Prior Publication Data

US 2003/0215448 A1 Nov. 20, 2003

Related U.S. Application Data

(63) Continuation-in-part of application No. 09/894,287, filed on Jun. 28, 2001, now Pat. No. 6,534,059.
(60) Provisional application No. 60/295,895, filed on Jun. 5, 2001.

(51) Int. Cl.⁷ ...................... A61K 39/395; A61K 39/40; A61K 39/42; A61K 39/44; A61K 38/21

(52) U.S. Cl. ................ 424/134.1; 424/158.1; 424/178.1; 424/141.1; 424/142.1; 424/145.1; 424/78.04; 424/85.4; 424/85.5; 514/912; 514/2; 530/388.1; 530/389.2; 530/388.23; 530/388.15; 530/387.1

(58) Field of Search .................. 424/134.1, 145.1, 424/178.1, 141.1, 85.4, 130.1, 85.5, 158.1, 78.04, 142.1; 514/912, 2; 530/388.1, 389.2, 388.23, 388.15, 387.1

(56) References Cited

U.S. PATENT DOCUMENTS

| | | | |
|---|---|---|---|
| 4,704,362 A | 11/1987 | Itakura et al. | |
| 5,759,808 A | 6/1998 | Casterman et al. | |
| 5,800,988 A | 9/1998 | Casterman et al. | |
| 5,840,526 A | 11/1998 | Casterman et al. | |
| 5,888,511 A | 3/1999 | Skurkovich et al. | |
| 6,015,695 A | 1/2000 | Casterman et al. | |
| 6,036,956 A * | 3/2000 | Jacob et al. ............. | 424/145.1 |
| 6,180,370 B1 | 1/2001 | Queen et al. | |
| 6,534,059 B2 * | 3/2003 | Skurkovich et al. ..... | 424/158.1 |
| 2002/0182212 A1 * | 12/2002 | Skurkovich et al. ..... | 424/145.1 |
| 2003/0215448 A1 * | 11/2003 | Skurkovich et al. ..... | 424/145.1 |
| 2003/0224005 A1 * | 12/2003 | Skurkovich et al. ..... | 424/184.1 |

FOREIGN PATENT DOCUMENTS

WO  WO 87/02671  5/1987

OTHER PUBLICATIONS

Nguyen et al, Molecular Immunology, 1999, 36:515–524.*
Avunduk et al, am. J. Opthalmol. 2003, 136:593–602.*
Teng et al, Blood Cells, Molecules, and Diseases, Jun. 2000, 26/3:177–185 (abstract only).*
Krause et al, Am. J. Med., 2003, 115:390–397.*
Cogne et al, Res. Immunol. 1989, 140:487–502.*
Wahner–Roedler et al, Medicine, 2003, 82/4:236–250.*
Tarrant et al, J. Exp. Med., 1999, 189/2:219–230.*
Egwuagu et al, J. Immunol., 1999, 162:510–517.*
Tarrant et al, J. Immunol., 1998, 161:122–127.*
Silver et al, J. Immunol., 2000, 165:5041–5047.*
Hooks et al, J. Neuroimmunol., 1990, 26/3:245–250 Abstract only.*
Dekaris et al, Croat. Med. J., 2001, 42/6:650–656 Abstract only.*
Yang et al, Br. J. Ophthalmol., 82/6:695–699 Abstract only.*
Signh et al, Immunol. Res., 2001, 23/1:59–74.*
Hu et al, Cell Research, 2001, 11/4:293–300 Abstract only.*
Wu et al, J. Neuroimmunol., 2003, 137/1–2:154–163 Abstract only.*
Hooks et al, Invest. Ophthalmol. Vis. Sci., 1988, 29:1444–1451.*
de Kozak et al, Intern. Immunol., 2002, 21:231–253.*
Kotter et al, clinical and Experimental Rheumatology, 1996, 14:313–315.*
Lacomba et al, Arch. Ophthalmol., 2000, 118:768–772.*
Atalla et al, Elsevier Science Publishers (Biomedical Division), Ocular Immunology Today, eds. Usui et al, 1990, pp. 65–68.*
Kijlstra, Eye, 1997, 11/Pt. 2:200–205.*
Skurkovich et al, Curr. Opin. Mol. Ther., 2003, 5/1:52–57 Abstract only.*
Bird et al., 1988, Science 242:423–426 (1988).
Feldman et al., "Interferons and Autoimmunity", IFN γ, p. 75, Academic Press (1987).
Gillam and Smith, Gene 8: 81–97 (1979).
Gringeri et al., Cell. Mol. Biol. 41 (3): 381–387 (1995).
Gringeri et al., J. Acquir. Immunol. Defic. Syndr. 13:55–67 (1996).
Gu et al., Thrombosis and Hematocyst, 77 (4):755–759 (1997).
Hamers–Casterman et al., Nature 363: 446–448 (1993).
Huston et al., Proc. Natl. Acad. Sci. USA 85: 5879–5883 (1988).
Queen et al., Immunol. Rev. 89: 49–68 (1986).
Roberts et al., Nature 328: 731–734 (1979).
Sastry et al., Proc. Nat'l Acad. Sci. USA, 86: 5728 (1989).
Seligmann et al., Immunological Rev. 48: 145–167 (1979).

(List continued on next page.)

*Primary Examiner*—N. M. Minnifield
(74) *Attorney, Agent, or Firm*—Morgan, Lewis & Bockius, LLP

(57) ABSTRACT

The present invention comprises and utilizes methods and compositions for treating hyperimmune reactions in the eye. Compositions comprising antibodies to gamma interferon alone and in combination with other drugs are described. Also disclosed in the invention are methods of applying a composition comprising interferon gamma antibodies topically to the eye to treat hyperimmune reactions, such as transplant rejection, uveitis, autoimmune diseases of the eye, and ocular disorders incidental to or connected with autoimmune diseases.

5 Claims, No Drawings

OTHER PUBLICATIONS

Skurkovich et al., Annals of Allergy, 35: 356 (1975).
Skurkovich et al., J. Interferon Res. 12, Suppl. 1:S110 (1992).
Skurkovich et al., Med. Hypoth., 41: 177–185 (1993).
Skurkovich et al., Med. Hypoth., 42: 27–35 (1994).
Skurkovich et al., Nature 217: 551–552 (1974).
Tuszynski et al., Blood, 72:109–115 (1988).
Ward et al., Nature 341: 544–546 (1989).

* cited by examiner

COMPOSITIONS AND METHODS FOR TREATING HYPERIMMUNE RESPONSE IN THE EYE

CROSS-REFERENCE TO RELATED APPLICATIONS present application is a continuation-in-part of U.S. application Ser. No. 09/894,287, filed on Jun. 28, 2001, now U.S. Pat. No. 6,534,059, which in turn claims priority from U.S. Provisional Application No. 60/295,895, filed on Jun. 5, 2001.

BACKGROUND OF THE INVENTION

The ability of the mammalian immune system to recognize "self" versus "non-self" antigens is vital to successful host defense against invading microorganisms. "Self" antigens are those which are not detectably different from an animal's own constituents, whereas "non-self" antigens are those which are detectably different from or foreign to the mammal's constituents. A normal mammalian immune system functions to recognize "non-self antigens" and attack and destroy them. An autoimmune disorder such as for example, rheumatoid arthritis, insulin-independent diabetes mellitus, acquired immune deficiency syndrome (AIDS), multiple sclerosis, and the like, results when the immune system identifies "self" antigens as "non-self", thereby initiating an immune response against the mammal's own body components (i.e., organs and/or tissues). This creates damage to the mammal's organs and/or tissues and can result in serious illness or death.

Predisposition of a mammal to an autoimmune disease is largely genetic; however, exogenous factors such as viruses, bacteria, or chemical agents may also play a role. Autoimmunity can also surface in tissues that are not normally exposed to lymphocytes such as for example, neural tissue and the eye (particularly the lens or the cornea). When a tissue not normally exposed to lymphocytes becomes exposed to these cells, the lymphocytes may recognize the surface antigens of these tissues as "non-self" and an immune response may ensue. Autoimmunity may also develop as a result of the introduction into the animal of antigens which are sensitive to the host's self antigens. An antigen which is similar to or cross-reactive with an antigen in an mammal's own tissue may cause lymphocytes to recognize and destroy both "self" and "non-self" antigens.

It has been suggested that the pathogenesis of autoimmune diseases is associated with a disruption in synthesis of interferons and other cytokines often induced by interferons (Skurkovich et al., Nature 217:551–552, 1974; Skurkovich et al., Annals of Allergy, 35:356, 1975; Skurkovich et al., J. Interferon Res. 12, Suppl. 1:S110, 1992; Skurkovich et al., Med. Hypoth., 41:177–185, 1993; Skurkovich et al., Med. Hypoth., 42:27–35, 1994; Gringeri et al., Cell. Mol. Biol. 41(3):381–387, 1995; Gringeri et al., J. Acquir. Immun. Defic. Syndr., 13:55–67, 1996). In particular, interferon (IFN) gamma plays a significant pathogenic role in autoimmune dysfunction. IFN gamma stimulates cells to produce elevated levels of HLA class II antigens (Feldman et al., 1987, "Interferons and Autoimmunity", In: IFN γ, p. 75, Academic Press). It is known that IFN gamma participates in the production of tumor necrosis factor (TNF), and it is also known that TNF also plays a role in stimulation of production of autoantibodies. In view of this, therapies to modulate these cytokines have been developed. Clinical success in treating several autoimmune diseases using antibodies to IFN gamma has been reported (Skurkovich et al., U.S. Pat. No. 5,888,511).

However, while an autoimmune response is considered to be typical in diseases such as multiple sclerosis and rheumatoid arthritis, one area of medicine where treatment of autoimmune or hyperimmune responses has not been fully explored is the area of transplant therapy. Autoimmunity arising from transplant rejection is typical in transplant patients. Rejection of a transplant is the organism's normal reaction to invading foreign antigens. In particular, transplantation of tissues or organs such as the eye, which is not normally exposed to lymphocytes, skin, heart, kidney, liver, bone marrow, and other organs, have a high rate of rejection, which rejection is largely the result of a hyperimmune reaction.

Hyperimmune reactions including rejection of tissue transplants in the eye are of considerable concern. Corneal transplants, lens replacements, and the like, are frequently rejected when transplanted into a human patient. In addition, other diseases in the eye, such as for example, keratoconjunctivitis sicca (dry eye syndrome), episcleritis, scleritis, Mooren's ulcer, ocular cicatricial pemphigoid, orbital pseudotumor, iritis, central serous retinopathy, Graves' ophthalmopathy, chorioretinitis, Sjogren's syndrome, uveitis, and Stevens-Johnson syndrome may also be the result of a hyperimmune reaction in the eye. Systemic infections, such as tuberculosis, syphilis, AIDS, toxoplasmosis infection, and cytomegalovirus retinitis, may also cause eye diseases, including but not limited to, uveitis, enophthalmitis, retinitis, choroiditis, and retinal necrosis. These types of hyperimmune reactions typically result in blurred vision and eventually blindness. Current therapies to treat such hyperimmune responses include corticosteroid treatment, including dexamethasone, and treatment with an anti-inflammatory preparation. To date, there are no successful or long-term methods or compositions for effectively treating hyperimmune reactions in the mammalian eye and other organs.

Of the above-mentioned hyperimmune responses in the eye, uveitis poses a significant threat to the eyesight of an afflicted patient. Uveitis is a general condition describing the inflammation of all or a portion of the uvea, the continuous layer of fibrous tissue that surrounds the eye. The uvea comprises the iris, the ciliary body, and the choroid. The iris is the circular, colored portion of the eye, the ciliary body is a thick ring of tissue that helps control the shape of the lens and is connected to both the iris and to the front portion of the choroid. The choroid is a membrane full of blood vessels that surrounds the eye. It extends from the ciliary body to the connection of the optic nerve with the back of the eye. Anterior uveitis (iritis) affects the front portion of the eye, intermediate uveitis (cyclitis) affects the ciliary body, and posterior uveitis (choroiditis) affects the back portion of the uvea. Diffuse uveitis affects all portions of the uvea.

Anterior uveitis commonly occurs in conjunction with juvenile rheumatoid arthritis, but does not manifest in all juvenile arthritis patients. Uveitis is most likely to be present in juvenile arthritis patients with pauciarticular disease (fewer than five joints involved), a positive anti-nuclear antibody test, and a negative rheumatoid factor test.

Although uveitis is a documented autoimmune disease, the mechanism leading to inflammation of the uvea is unknown. Uveitis is a secondary manifestation of many autoimmune and infectious diseases, such as ankylosing spondylitis, juvenile rheumatoid arthritis, sarcoidosis, toxoplasmosis, herpes, syphilis, and cytomegalovirus infection. However, the etiology is not known in from about 33% to about 50% of uveitis cases. No known racial predilection for uveitis exists, but in juveniles, the disease appears in girls approximately four times more often than boys.

The symptoms of uveitis can vary depending on the location of the uveitis; acute and severe symptoms are generally more common in anterior uveitis and can include: eye pain, eye redness, photophobia, blurred or decreased vision and blindness. Other symptoms include "floaters" which are small specks or clouds that move with the field of vision, chronic flare in the eye, band keratopathy, secondary glaucoma and posterior subcapsular cataracts.

The morbidity and mortality of uveitis are often related to two extremes of treatment, either lack thereof or overzealous treatment. Mortality more often results from the latter. Standard treatments include both medical and surgical treatments. Surgical intervention is reserved for chelating treatment in addressing the problems associated with band keratopathy and cataract or glaucoma surgery, if the disease should progress to such a point. Medical intervention is the most common method of addressing the initial symptoms of uveitis and resulting sequelae. Medical treatments are divided into four major categories, and are used depending on the state of the disease, the patient's overall health and age, and other factors well known to one of ordinary skill in the art.

Topical corticosteroids are the primary form of medical treatment for uveitis. Prednisone is often the first line drug administered to a patient afflicted with uveitis, but may result in increased intraocular pressure or cataracts with long-term use, as well as the immunosuppression and other side effects common to corticosteroids. Triamcinolone acetonide is often administered as a periocular injection for more severe cases of uveitis, but infections, edema, osteoporosis, psychosis and growth suppression are often noted as side effects of this particular treatment.

Treatment of uveitis can also consist of corticosteroid administration in conjunction with chronic dilation until the inflammation is resolved. Corticosteroid therapy may be topical (eye-drops), injected adjacent to the eye, or even oral in uveitis cases refractory to topical or injected steroids.

Cycloplegics are used to block nerve impulses to the pupillary sphincter and ciliary muscles, which serve to ease the pain and photophobia of uveitis. Cyclopentolate and homatropine hydrobromide are both commonly used cycloplegics, but carry the risk of increased intraocular pressure as well as systemic toxic anticholinergic effects.

Nonsteroidal anti-inflammatory drugs (NSAIDs) are used in the treatment of uveitis to reduce pain and inflammation. While they often do not exhibit the risks and side effects of the above mentioned drugs, chronic and regular use of NSAIDs is required to manage the inflammation of uveitis, and they are not as effective as corticosteroids.

Finally, severe cases of uveitis are sometimes treated with systemic immunosuppressive drugs, often as a second line drug in conjunction with corticosteroids. Methotrexate, cyclosporine A, cyclophosphamide and chlorambucil are the most commonly used immunosuppressive drugs in the treatment of uveitis. The major drawbacks when using these drugs range from renal and liver failure, anemia and chromosome damage to susceptibility to bacterial, viral and fungal infections.

There exists a long felt need to develop safe and effective therapies for treating hyperimmune responses of the eye, especially hyperimmune responses such as uveitis. The present invention meets this need.

SUMMARY OF THE INVENTION

The invention includes a method of treating uveitis in a patient. The method comprises administering to the patient an effective amount of an antibody to gamma interferon.

In one aspect, the antibody is selected from the group consisting of a polyclonal antibody, a biologically active fragment thereof, an allelic variant thereof, a species variant thereof, a monoclonal antibody, a biologically active fragment thereof, an allelic variant thereof, a species variant thereof, a humanized antibody, a biologically active fragment thereof, an allelic variant thereof, a species variant thereof, a synthetic antibody, a biologically active fragment thereof, an allelic variant thereof, a species variant thereof, a heavy chain antibody, and combinations thereof.

In another aspect of the present invention, the antibody is administered intramuscularly, intravenously, intradermally, cutaneously, ionophoretically, topically, and locally.

In yet another aspect of the invention, the antibody is selected from the group consisting of a polyclonal antibody, a monoclonal antibody, a synthetic antibody, a heavy chain antibody and a humanized antibody.

In still another aspect of the present invention, the heavy chain antibody is selected from the group consisting of a camelid antibody, a heavy chain disease antibody, and a variable heavy chain immunoglobulin.

DETAILED DESCRIPTION OF THE INVENTION

The invention comprises and utilizes the discovery that administration of antibodies to interferon (IFN) gamma to an animal having an autoimmune reaction in the eye is useful in alleviating or eliminating the autoimmune reaction. Such autoimmune reactions in the eye may occur as a result of transplants of eye tissue and eye diseases, including but not limited to Sjogren's syndrome, multiple sclerosis, sarcoidosis, ankylosing spondylitis, keratoconjunctivitis sicca (dry eye syndrome), episcleritis, scleritis, Mooren's ulcer, ocular cicatricial pemphigoid, orbital pseudotumor, iritis, central serous retinopathy, Graves' ophthalmopathy, chorioretinitis, Stevens-Johnson syndrome, uveitis, enophthalmitis, retinitis, choroiditis, and retinal necrosis. Autoimmune reactions in the eye may also occur as a result of contracting an infectious disease, including, but not limited to AIDS, syphilis, toxoplasmosis infection, and tuberculosis. Autoimmunity may also occur as a result of transplantation of tissue into the eye.

It is immediately apparent from the Examples disclosed herein that antibodies to IFN gamma are also useful for treatment of eye diseases which are characterized by hemorrhage and exudate collection in the eye. Hemorrhage and/or exudate may collect in the anterior chamber of the eye and is a characteristic result of an inflammatory reaction. Typically, these symptoms occur during transplant rejection (i.e., a hyperimmune response). However, the invention should not be construed as being limited solely to the examples provided herein, as other autoimmune diseases of the mammalian eye which are at present unknown, once known, may also be treatable using the methods of the invention. As a non-limiting example, the data disclosed elsewhere herein demonstrate, for the first time, that the methods of the present invention are useful for treating uveitis.

The invention includes a method of treating an eye disease characterized by a hyperimmune response in the eye of a mammal. Briefly, the method comprises applying antibodies to gamma interferon directly to the affected eye. The method can be used to treat an autoimmune eye disease in any mammal; however, preferably, the mammal is a human.

The antibodies to interferon gamma useful in the methods of the invention may be polyclonal antibodies, monoclonal antibodies, synthetic antibodies, such as a biologically active fragment of an antibody to interferon gamma, or they may be humanized monoclonal antibodies. Methods of making and using each of the types of antibodies useful in the methods of the invention are now described. In addition, human antibodies to interferon gamma, obtained from human donors, may be employed in the invention. The present invention further contemplates the use of heavy chain antibodies, including, but not limited to antibodies derived from camelid species, and other heavy chain antibodies as detailed extensively elsewhere herein. Preparation of antibodies which are useful in the present invention is more fully discussed below.

When the antibody used in the methods of the invention is a polyclonal antibody (IgG), the antibody is generated by inoculating a suitable animal with interferon gamma or a fragment thereof. Antibodies produced in the inoculated animal which specifically bind interferon gamma are then isolated from fluid obtained from the animal. Interferon gamma antibodies may be generated in this manner in several non-human mammals such as, but not limited to goat, sheep, horse, rabbit, and donkey. Methods for generating polyclonal antibodies are well known in the art and are described, for example in Harlow, et al. (1988, In: Antibodies, A Laboratory Manual, Cold Spring Harbor, N.Y.). These methods are not repeated herein as they are commonly used in the art of antibody technology.

When the antibody used in the methods of the invention is a monoclonal antibody, the antibody is generated using any well known monoclonal antibody preparation procedures such as those described, for example, in Harlow et al. (supra) and in Tuszynski et al. (1988, Blood, 72:109–115). Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of interferon gamma may be prepared using the techniques described in Harlow, et al. (supra).

When the antibody used in the methods of the invention is a biologically active antibody fragment or a synthetic antibody corresponding to antibody to interferon gamma, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3,4):125–168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art.

The present invention also includes the use of humanized antibodies specifically reactive with IFN gamma epitopes. These antibodies are capable of neutralizing human IFN gamma. The humanized antibodies of the invention have a human framework and have one or more complementarity determining regions (CDRs) from an antibody, typically a mouse antibody, specifically reactive with IFN gamma. Thus, the humanized gamma IFN antibodies of the present invention are useful in the treatment of eye diseases and diseases of other organs which are characterized by an autoimmune reaction which includes overproduction of interferon gamma.

When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755–759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as human IFN gamma, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671. CDRs useful in producing the antibodies of the present invention may be similarly derived from DNA encoding monoclonal antibodies capable of binding to human IFN gamma. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources such as the American Type Culture Collection , Manassas, Va.

In addition to the humanized IFN gamma discussed above, other "substantially homologous" modifications to native IFN gamma antibody sequences can be readily designed and manufactured utilizing various recombinant DNA techniques well known to those skilled in the art. Moreover, a variety of different human framework regions may be used singly or in combination as a basis for humanizing antibodies directed at IFN gamma. In general, modifications of genes may be readily accomplished using a variety of well-known techniques, such as site-directed mutagenesis (Gillman and Smith, Gene, 8, 81–97 (1979); Roberts et al., 1987, Nature, 328, 731–734).

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446–448). Such heavy-chain antibodies are useful in that they are smaller than conventional mammalian antibodies, they are more soluble than conventional antibodies, and further demonstrate an increased stability compared to some other antibodies.

Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The use of Old World and New World camelids for the production of antibodies is contemplated in the present invention, as are other methods for the production of camelid antibodies set forth herein.

The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species with no undue experimentation. As an example, the production of antibodies in mammals is detailed in such references as Harlow et al., (1989, Antibodies: A Laboratory Manual, Cold Spring Harbor, N.Y.). Camelid species for the production of antibodies and sundry other uses are available from various sources, including but not limited to, Camello Fataga S. L. (Gran Canaria, Canary Islands) for Old World camelids, and High Acres Llamas (Fredricksburg, Tex.) for New World camelids.

The isolation of camelid antibodies from the serum of a camelid species can be performed by many methods well known in the art, including but not limited to ammonium sulfate precipitation, antigen affinity purification, Protein A and Protein G purification, and the like. As an example, a camelid species may be immunized to a desired antigen, for example an interferon gamma, IL-1, or tumor necrosis factor alpha peptide, or fragment thereof, using techniques well known in the art. The whole blood can them be drawn from the camelid and sera can be separated using standard techniques. The sera can then be absorbed onto a Protein G-Sepharose column (Pharmacia, Piscataway, N.J.) and washed with appropriate buffers, for example 20 mM phosphate buffer (pH 7.0). The camelid antibody can then be eluted using a variety of techniques well known in the art, for example 0.15M NaCl, 0.58% acetic acid (pH 3.5). The efficiency of the elution and purification of the camelid antibody can be determined by various methods, including SDS-PAGE, Bradford Assays, and the like. The fraction that is not absorbed can be bound to a Protein A-Sepharose column (Pharmacia, Piscataway, N.J.) and eluted using, for example 0.15M NaCl, 0.58% acetic acid (pH 4.5). The skilled artisan will readily understand that the above methods for the isolation and purification of camelid antibodies are exemplary, and other methods for protein isolation are well known in the art and are encompassed in the present invention.

The present invention further contemplates the production of camelid antibodies expressed from nucleic acid. Such methods are well known in the art, and are detailed in, for example U.S. Pat. Nos. 5,800,988; 5,759,808; 5,840,526; and 6,015,695, which are incorporated herein by reference in their entirety. Briefly, cDNA can be synthesized from camelid spleen mRNA. Isolation of RNA can be performed using multiple methods and compositions, including TRIZOL (Gibco/BRL, La Jolla, Calif.) further, total RNA can be isolated from tissues using the guanidium isothiocyanate method detailed in, for example, Sambrook et al. (1989, Molecular Cloning, A Laboratory Manual, Cold Spring Harbor, N.Y.). Methods for purification of mRNA from total cellular or tissue RNA are well known in the art, and include, for example, oligo-T paramagnetic beads. cDNA synthesis can then be obtained from mRNA using mRNA template, an oligo dT primer and a reverse transcriptase enzyme, available commercially from a variety of sources, including Invitrogen (La Jolla, Calif.). Second strand cDNA can be obtained from mRNA using RNAse H and *E. coli* DNA polymerase I according to techniques well known in the art.

Identification of cDNA sequences of relevance can be performed by hybridization techniques well known by one of ordinary skill in the art, and include methods such as Southern blotting, RNA protection assays, and the like. Probes to identify variable heavy immunoglobulin chains ($V_{HH}$) are available commercially and are well known in the art, as detailed in, for example, Sastry et al., (1989, Proc. Nat'l. Acad. Sci. USA, 86:5728). Full-length clones can be produced from cDNA sequences using any techniques well known in the art and detailed in, for example, Sambrook et al. (1989, Molecular Cloning, A Laboratory Manual, Cold Spring Harbor, N.Y.).

The clones can be expressed in any type of expression vector known to the skilled artisan. Further, various expression systems can be used to express the $V_{HH}$ peptides of the present invention, and include, but are not limited to eukaryotic and prokaryotic systems, including bacterial cells, mammalian cells, insect cells, yeast cells, and the like. Such methods for the expression of a protein are well known in the art and are detailed elsewhere herein.

The $V_{HH}$ immunoglobulin proteins isolated from a camelid species or expressed from nucleic acids encoding such proteins can be used directly in the methods of the present invention, or can be further isolated and/or purified using methods disclosed elsewhere herein.

The present invention is not limited to $V_{HH}$ proteins isolated from camelid species, but also includes $V_{HH}$ proteins isolated from other sources such as animals with heavy chain disease (Seligmann et al., 1979, Immunological Rev. 48:145–167, incorporated herein by reference in its entirety). The present invention further comprises variable heavy chain immunoglobulins produced from mice and other mammals, as detailed in Ward et al. (1989, Nature 341:544–546, incorporated herein by reference in its entirety). Briefly, $V_H$ genes were isolated from mouse splenic preparations and expressed in *E. coli*. The present invention encompasses the use of such heavy chain immunoglobulins in the treatment of various autoimmune disorders detailed herein.

Substantially homologous sequences to IFN gamma antibody sequences are those which exhibit at least about 85% homology, usually at least about 90%, and preferably at least about 95% homology with a reference IFN gamma immunoglobulin protein.

Alternatively, polypeptide fragments comprising only a portion of the primary antibody structure may be produced, which fragments possess one or more functions of IFN gamma antibody. These polypeptide fragments may be generated by proteolytic cleavage of intact antibodies using methods well known in the art, or they may be generated by inserting stop codons at the desired locations in vectors comprising the fragment using site-directed mutagenesis.

DNA encoding antibody to IFN gamma is expressed in a host cell driven by a suitable promoter regulatory sequence which is operably linked to the DNA encoding the antibody. Typically, DNA encoding the antibody is cloned into a suitable expression vector such that the sequence encoding the antibody is operably linked to the promoter/regulatory sequence. Such expression vectors are typically replication competent in a host organism either as an episome or as an integral part of the host chromosomal DNA. Commonly, an expression vector will comprise DNA encoding a detectable marker protein, e.g., a gene encoding resistance to tetracycline or neomycin, to permit detection of cells transformed with the desired DNA sequences (U.S. Pat. No. 4,704,362).

*Escherichia coli* is an example of a prokaryotic host which is particularly useful for expression of DNA sequences encoding the antibodies of the present invention. Other microbial hosts suitable for use include but are not limited to, *Bacillus subtilis*, and other enterobacteriaceae, such as selected member of Salmonella, Serratia, and various Pseudomonas species. It is possible to generate expression vectors suitable for the desired host cell wherein the vectors will typically comprise an expression control sequence which is compatible with the host cell. A variety of promoter/regulatory sequences are useful for expression of genes in these cells, including but not limited to the lactose promoter system, a tryptophan (trp) promoter system, a beta-lactamase promoter system, or a promoter system derived from phage lambda. The promoter will typically control expression of the antibody whose DNA sequence is operably linked thereto, the promoter is optionally linked with an operator sequence and generally comprises RNA polymerase and ribosome binding site sequences and the like for initiating and completing transcription and translation of the desired antibody.

Yeast is an example of a eukaryotic host useful for cloning DNA sequences encoding the antibodies of the present invention. Saccharomyces is a preferred eukaryotic host. Promoter/regulatory sequences which drive expression of nucleic acids in eukaryotic cells include but are not limited to the 3-phosphoglycerate kinase promoter/regulatory sequence and promoter/regulatory sequences which drive expression of nucleic acid encoding other glycolytic enzymes.

In addition to microorganisms, mammalian tissue cell culture may also be used to express and produce the antibodies of the present invention (Winnacker, 1987, "From Genes to Clones," VCH Publishers, New York, N.Y.). Eukaryotic cells are preferred for expression of antibodies and a number of suitable host cell lines have been developed in the art, including Chinese Hamster Ovary (CHO) cells, various COS cell lines, HeLa cells, preferably myeloma cell lines, and transformed B-cells or hybridomas. Expression vectors which express desired sequences in these cells can include expression control sequences, such as an origin of DNA replication, a promoter, an enhancer (Queen et al., 1986, Immunol. Rev., 89, 49–68), and necessary processing sequence sites, such as ribosome binding sites, RNA splice sites, polyadenylation sites, and transcriptional initiation and terminator sequences. Preferred expression control sequences are promoters derived from immunoglobulin genes, Simian Virus (SV) 40, adenovirus, cytomegalovirus, bovine papilloma virus and the like.

The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (Sambrook et al., 1989, Molecular Cloning, A Laboratory Manual, Cold Spring Harbor, N.Y.).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used therapeutically.

The antibodies of the invention may be used in a therapeutic setting in a pharmaceutical acceptable carrier either alone, or they may be used together with a chemotherapeutic agent and/or standard therapy such as a non-steroidal anti-inflammatory drug, a corticosteroid, or an immunosuppressant. The antibodies, or complexes derived therefrom, can be prepared in a pharmaceutically accepted dosage form which will vary depending on the mode of administration.

The invention thus embodies a novel composition comprising antibodies that bind with IFN gamma for use in treatment of eye disease. As stated above, the antibodies can be monoclonal antibodies, polyclonal antibodies, humanized monoclonal antibodies, camelid antibodies, or monoclonal chimeric antibodies, or a biologically active fragment of any type of antibody herein recited. Generation of each type of antibody is discussed herein and applies to generation of antibodies for use in the novel methods of the invention. Generally, it is preferred that monoclonal humanized antibodies are used because they are non-immunogenic, and thus, will not elicit an immune response. However, any type of antibody may be used in the present invention.

The method of the invention is not intended to be limited to use of antibodies to IFN gamma. Inhibitors to IFN gamma are also useful in the method of the invention. Such inhibitors include, but are not limited to, peptides which block the function of IFN gamma, IFN gamma receptor and antibodies to IFN gamma receptors, and any combination thereof.

The pharmaceutical composition useful for practicing the invention may be administered to deliver a dose of between one microgram per kilogram per day and one hundred milligrams per kilogram per day.

Pharmaceutical compositions that are useful in the methods of the invention may be administered topically or systemically in ophthalmic, injectable, or other similar formulations. In addition to the antibodies to IFN gamma, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the gamma IFN antibodies according to the methods of the invention.

Compounds comprising antibodies to IFN gamma that can be pharmaceutically formulated and administered to an animal for treatment of autoimmune reactions in the eye are now described.

The invention encompasses the preparation and use of pharmaceutical compositions comprising antibodies to IFN gamma as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include IFN gamma receptor, antibodies to IFN gamma receptors, IFN beta, interleukin-10 (IL-10), and any combination thereof.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein. Ionophoretic administration of the pharmaceutical composition of the invention is considered a form of topical administration herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parenterally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for ophthalmic administration. Such formulations may, for example, be in the form of eye drops including, for example, a 0.1% to 1.0% (w/w) solution or suspension of the active ingredient in an aqueous or oily liquid carrier. Such drops may further comprise buffering agents, salts, or one or more other of the additional ingredients described herein. Other administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Preferably, the composition of the invention is administered topically. The composition may be administered as an ointment to the lower eyelid. Preferably, the composition is administered in the form of eye drops. However, the composition comprising antibody to IFN-gamma may also be administered parenterally.

The antibodies to IFN-gamma may be present in a composition to be administered to the affected eye at a range of concentrations. The concentration of IFN-gamma antibody present in the composition can be from about 0.1 mg/ml to about 500 mg/ml, preferably from about 1 mg/ml to about 300 mg/ml, even more preferably from about 5 mg/ml to about 200 mg/ml, yet more preferably from about 10 mg/ml to about 100 mg/ml, even more preferably from about 20 mg/ml to about 75 mg/ml, more preferably from about 25 mg/ml to about 50 mg/ml, even more preferably from about 30 mg/ml to about 35 mg/ml, even more preferably about 33 mg/ml.

A composition comprising an antibody to IFN gamma can be administered to the affected eye once a month, once every two weeks, once a week, several times a week, several times per day or once a day. Preferably, the composition is administered from one to five times per day, and more preferably, the composition is administered from one to three times per day. Most preferred is administration of the composition three times per day.

IFN gamma antibodies can be administered to the affected eye of a patient for as long as necessary to remedy the effects of the autoimmune reaction. Preferably, the patient receives treatment for about 5 to about 10 days. More preferably, the patient receives treatment for about 5 to about 7 days. The entire treatment of administering IFN gamma antibodies can be repeated several times.

As evidenced by the Examples, the present invention is particularly useful in treating a hyperimmune response resulting from rejection of an eye-related tissue or organ transplant. The invention is also useful in preventing an expected rejection of a transplanted tissue or organ when the composition of the invention is administered about one day before, during, and immediately after transplant surgery. The preferred treatment period is about seven days.

As further demonstrated by the data disclosed herein, the present invention is also particularly useful as a treatment for an autoimmune disease of the eye, including, but not limited to uveitis, and all forms thereof, as detailed elsewhere herein. That is, the data demonstrate that administration of an antibody to IFN gamma, or a fragment thereof, to a patient with uveitis can result in, inter alia, a shortened period of acute uveitis, an increased duration of remission, and a reduction in the severity of uveitis symptoms during the acute phase of the disease.

Administering IFN gamma antibodies to the an affected eye is also effective against damage of eye and optic nerve cells caused by hyperproduction of IFN gamma. Hyperproduction of IFN gamma can also induce an autoimmune response in the eye. Thus, the administration of IFN gamma antibodies to an eye affected with a disease that causes hyperproduction of IFN gamma is well within the purview of the present invention.

Definitions

The articles "a" and "an" are used herein to refer to one or to more than one (i.e. to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, camelid antibodies, heavy chain antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "biologically active antibody fragment" is meant a fragment of an antibody which retains the ability to specifically bind to IFN gamma.

A "disease" is a state of health of an animal wherein the animal cannot maintain homeostasis, and wherein if the disease is not ameliorated then the animal's health continues to deteriorate. Use of the term disease throughout the application is meant to encompass the terms diseases, disorders, and conditions.

"Treatment" of a disease occurs when the severity of a symptom of the disease, the frequency with which such a symptom is experienced by a patient, or both, is reduced or eliminated. "Treatment" also encompasses prevention of an anticipated disease state. For example, treatment of a transplant rejection includes use of a composition comprising antibodies to IFN gamma after rejection has already occurred, and also within a period of post-transplant surgery to prevent an anticipated rejection. The preferred period post-surgery is about seven days.

By the term "specifically binds," as used herein, is meant an antibody which recognizes and binds IFN gamma, but does not substantially recognize or bind other molecules in a sample.

"Autoimmune response" refers to an alteration in the immune system wherein the immune response mounted during a disease state is detrimental to the host. Typically, cells of the immune system or other immune system components such as antibodies produced by the host, recognize "self" antigens as foreign antigens.

A "hyperimmune response" refers to an autoimmune response characterized by an overexpression of one or more cytokines of the immune system.

As used here, "an eye-related tissue or organ" refers to the tissues and organs that constitute the eye. These include all parts of the eye as would be classified in an anatomy textbook, for example, Williams et al., eds., 1980, Gray's-Anatomy, 36th ed., W. B. Saunders Co., Philadelphia.

A "corneal transplant" refers to the insertion of a cornea into the eye of a mammal, where the cornea being inserted is not the natural cornea of the mammal. The cornea being inserted may be from a cadaver.

As used herein, the term "heavy chain antibody" or "heavy chain antibodies" comprises immunoglobulin molecules derived from camelid species, either by immunization with an peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

A pharmaceutical composition is said to be "topically administered" when it is applied directly to the affected area. Eye drops, for example, are applied topically, as are creams and ointments. Ionophoresis is also included as a form of topical administration.

The term "standard therapy" as used herein refers to drugs and other therapeutics used in the treatment of uveitis, and includes, but is not limited to, steroids, topical steroids, corticosteroids, topical corticosteroids, cycloplegics, nonsteroidal anti-inflammatory drugs, immunosuppresive drugs, systemic immunosuppressive drugs, anti-inflammatories, antibiotics, vitamins, or any combination thereof.

"Recombinant DNA" refers to a polynucleotide having sequences that are not naturally joined together. An amplified or assembled recombinant polynucleotide may be included in a suitable vector, and the vector can be used to transform a suitable host cell. A recombinant DNA polynucleotide may serve a non-coding function (e.g., promoter, origin of replication, ribosome-binding site, etc.) as well.

"Uveitis", as used herein, refers to all forms of inflammation of the uvea, including but not limited to rheumatoid uveitis, anterior uveitis (iridocyclitis or iritis), intermediate uveitis (cyclitis), posterior uveitis (choroiditis) and diffuse uveitis.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

In each of the transplant rejection trials reported below, the concentration of Fab2 fragments of antibody was 50 mg/ml of protein. The anti-IFN gamma activity when measured by ELISA exhibited a significant signal at a dilution of 1:10,000. The fragments were in liquid form. The liquid formulation of antibody fragments was administered at two to three drops per eye, three times per day for seven to ten days. Improvements in visual acuity and other signs were noted often by the second or third day after administration of the drops.

Clinical trials were conducted with on three patients who had recently undergone corneal transplant surgery. Patient G, male, fifty-three years of age, underwent corneal transplantation to treat keratoconus. The surgery included extraction of a cataract and implantation of an artificial lens. Patient G subsequently had a transplant rejection reaction characterized by deteriorating vision and opacity of the corneal transplant. Patient G was treated with standard therapy without therapeutic effect. Standard therapies may include, but are not limited to, steroids, topical steroids, corticosteroids, topical corticosteroids, cycloplegics, nonsteroidal anti-inflammatory drugs, immunosuppresive drugs, systemic immunosuppressive, anti-inflammatories, antibiotics, vitamins, or any combination thereof, administered either topically, in the form of drops or ointment, or intravenously, by injection under the conjunctiva, orally, and intramuscularly. Fragments of goat anti-human interferon gamma antibodies were administered to the affected eye in the form of eye drops on an outpatient basis. The drops were administered at two drops three times daily, over a period of seven days. Patient G exhibited a significant improvement in visual acuity after two days of treatment. Further, the corneal transplant reverted from opacity to almost complete transparency and peripheral areas of the cornea became significantly more transparent as well.

Patient P, male, thirty-nine years of age, underwent corneal transplantation to treat keratoconus in 1999. Nine months later, Patient P was diagnosed with a transplant rejection reaction and was treated with twenty-five doses of dexamethasone, both intravenously and using eye drops. Patient P received other types of therapy as well, and continued treatment on an outpatient basis. Six months after the first transplant rejection, Patient P was diagnosed with a second transplant rejection reaction. Patient P was treated on an outpatient basis with the same therapy used for the first rejection. One month later, Patient P's previous therapy was discontinued and treatment with antibodies to interferon gamma in the form of eye drops was initiated. One day later, Patient P experienced improvement in visual acuity and the transplanted cornea became more transparent in peripheral areas. Over the next two days of treatment, Patient P exhibited complete corneal transparency and a drastic improvement of vision.

Patient F, female, fifty-three years of age, underwent corneal transplantation and extraction of a cataract to treat a purulent corneal ulcer and herpes zoster. Ten days later, the transplant was rejected. Patient F underwent another corneal transplantation thirteen days after rejection of the first transplant. Patient F received therapy with multiple antibiotics, steroids, anti-inflammatory preparations, and atropine. Despite all therapies administered, Patient F persistently displayed a purulent ring around the transplant, the transplant itself was cloudy, and the anterior eye chamber was hemorrhaging and was filled with exudate. Patient F's affected eye was treated with antibodies to interferon gamma in the form of eye drops, administered at 2 drops three times daily. After three days of administration, Patient F's condition improved. The purulent ring around the transplant significantly cleared and became white and the cornea became significantly more transparent. Exudate and hemorrhage in the anterior chamber completely disappeared, and the affected eye appeared significantly normal.

The results of the experiments disclosed establish that treatment of hyperimmune disease of the eye with antibody to IFN gamma is effective.

Treatment of Uveitis

Standard therapy used in the present trial comprised subconjunctival injections of corticosteroids (e.g. dexamethasone, 0.3 cc for young children, 0.5 cc for older children. Further, corticosteroids were administered as eye drops (dexamethasone 1 mg/ml). When eye drops are used in place of subconjunctival injections, drops are administered very frequently (every 5 minutes for 1–2 hours). Non-steroidal anti-inflammatory preparations (diclofenac 0.1% solution, a.k.a VOLTAREN OPTHALMIC, Novartis, East Hanover, N.J.) are administered according to the same schedule as dexamethasone drops. In addition, proteolytic enzyme inhibitors (contrical, GORDOX, aprotinin, a.k.a TRASYLOL, Bayer, Pittsburgh, Pa.) are administered as 1 drop 6–8 times per day at a concentration of 100,000 units per milliliter.

Standard therapy used in the present trial further comprises the administration of mydriatics (pupil dilators and cholinergic antagonists) and ACTOVEGIN (Nycomed Pharma, Roskilde, Denmark) according to the manufacturers directions.

Anti-IFN-gamma antibodies were produced by immunizing goats with recombinant human IFN-gamma (Peprotech, Rocky Hill, N.J.) using methods well known in the art. Goats were plasmapheresed and the IgG was isolated. F(ab')2 fragments were prepared by pepsin digestion and purified by gel filtration. Protein concentration was 33 mg/ml with an IFN-gamma neutralizing activity of >66 µg/ml as determined by a cell growth inhibition assay well known in the art.

In the present trial, 1 drop (approximately 40 microliters) of the anti-IFN-gamma antibodies described above were administered to the patient every two hours while the patient was awake for five consecutive days.

The acute phase and flare-ups of uveitis were measured in the present study using methods well known in the art, including symptoms such as increased clouding of the cornea, appearance of precipitates and new synechiae (a disease of the eye in which the iris adheres to the cornea or capsule of the lens).

Clinical signs of the remission of uveitis were measured using clinical parameters such as disappearance of corneal clouding, absence of vasodilation in the iris. Further, a diminished amount of precipitates and synechiae indicate remission, however, precipitates and synechiae may still be present.

Clinical trials were conducted on six patients ranging from 2.5 years to 7 years of age, all of which were diagnosed with juvenile rheumatoid arthritis and uveitis. When comparing standard therapy plus antibodies to IFN gamma with standard therapy alone, treatment of patients with standard therapy in addition to drops of anti-IFN gamma antibodies resulted in a 3-fold reduction of the duration of the patient's acute period of uveitis, a substantial increase in the length of remission, and a reduction in the severity of the symptoms during the acute period and an decreased time in the transition from acute uveitis to remission.

Table 1 depicts the duration of uveitis remission since treatment with anti-IFN gamma antibodies and standard therapy.

TABLE 1

| Patient | Length of Remission | Notes |
|---------|---------------------|-------|
| 1 | 11 months | Continuing, no flare-ups |
| 2 | 8 months | Continuing |
| 3 | 3 months | Monthly flare-ups before therapy |
| 4 | 1 month | Continuing, no flare-ups |
| 5 | 6 months | Continuing |
| 6 | | No Response |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating uveitis in a patient, the method comprising administering to said patient a combination of an effective amount of an antibody to gamma interferon and standard therapy.

2. The method of claim 1, wherein said antibody is selected from the group consisting of a polyclonal antibody, a monoclonal antibody, a humanized antibody, a synthetic antibody, a heavy chain antibody, a biologically active fragment of an antibody, wherein said biologically active fragment comprises an Fv fragment, an Fab fragment or an F(ab)$_2$ fragment, and combinations thereof.

3. The method of claim 1, wherein said antibody is administered by the route selected from the group consisting of intramuscularly, intravenously, intradermally, cutaneously, ionophoretically, topically, and locally.

4. The method of claim 1, wherein said antibody is selected from the group consisting of a polyclonal antibody, a monoclonal antibody, a synthetic antibody, a heavy chain antibody and a humanized antibody.

5. The method of claim 4, wherein said heavy chain antibody is selected from the group consisting of a camelid antibody, a heavy chain disease antibody, and a variable heavy chain immunoglobulin.

* * * * *